United States Patent [19]

Brandes

[11] Patent Number: 5,618,846
[45] Date of Patent: Apr. 8, 1997

[54] TREATMENT METHOD FOR CANCER

[75] Inventor: Lorne J. Brandes, Winnipeg, Canada

[73] Assignee: University of Manitoba, Winnipeg, Canada

[21] Appl. No.: 458,847

[22] Filed: Jun. 2, 1995

Related U.S. Application Data

[60] Division of Ser. No. 82,785, Jun. 28, 1993, which is a continuation-in-part of Ser. No. 711,975, Jun. 7, 1991, abandoned, which is a continuation-in-part of Ser. No. 627,863, Dec. 17, 1990, abandoned.

[30] Foreign Application Priority Data

Feb. 17, 1993 [GB] United Kingdom ............... 9303210

[51] Int. Cl.$^6$ ............................................... A61K 31/135
[52] U.S. Cl. ............................................................... 514/641
[58] Field of Search .............................. 514/34, 648, 651

[56] References Cited

U.S. PATENT DOCUMENTS

| 4,803,227 | 2/1989 | Brandes et al. | 514/651 |
| 4,829,068 | 5/1989 | Brandes et al. | 514/648 |

OTHER PUBLICATIONS

Anticancer Research 6:451 to 464 (1986), Robert C. Warrington.

"Histamine is an Intracellular Messenger Mediating Platelet Aggregation" by Saxena et al, Science, vol. 243; pp. 1596–1599; (1993).

The Merck Index, 9th Edition, Merck & Co., Inc. Rahway, N.J., U.S.A., 1976; p. 456 (WO3428).

*Primary Examiner*—James H. Reamer

[57] ABSTRACT

The in vivo chemotherapeutic treatment of cancer cells in a living animal is improved by first administering to the animal, a compound which inhibits normal cell proliferation while promoting malignant cell proliferation, specifically a potent antagonist selective for intracellular histamine receptors, in an amount sufficient to inhibit the binding of intracellular histamine to the receptors in normal and malignant cells. An enhanced toxic effect on the cancer cells from the chemotherapeutic agent is obtained while any adverse effect of the chemotherapeutic agent on normal cells, particularly bone marrow and gastro-intestinal cells, is inhibited. In addition, long term continuous administration of the antagonist following administration of the chemotherapeutic agent results in at least amelioration of adverse side effects of chemotherapy on normal bone marrow and gastro-intestinal cells. The treatment of cancer cells using DPPE in combination with the chemotherapeutic agents specifically illustrates the invention.

6 Claims, 11 Drawing Sheets

Tumor Growth Promotion (Murine C-3 Fibrosarcoma)
By a Human-Equivalent Daily Dose of Astemizole
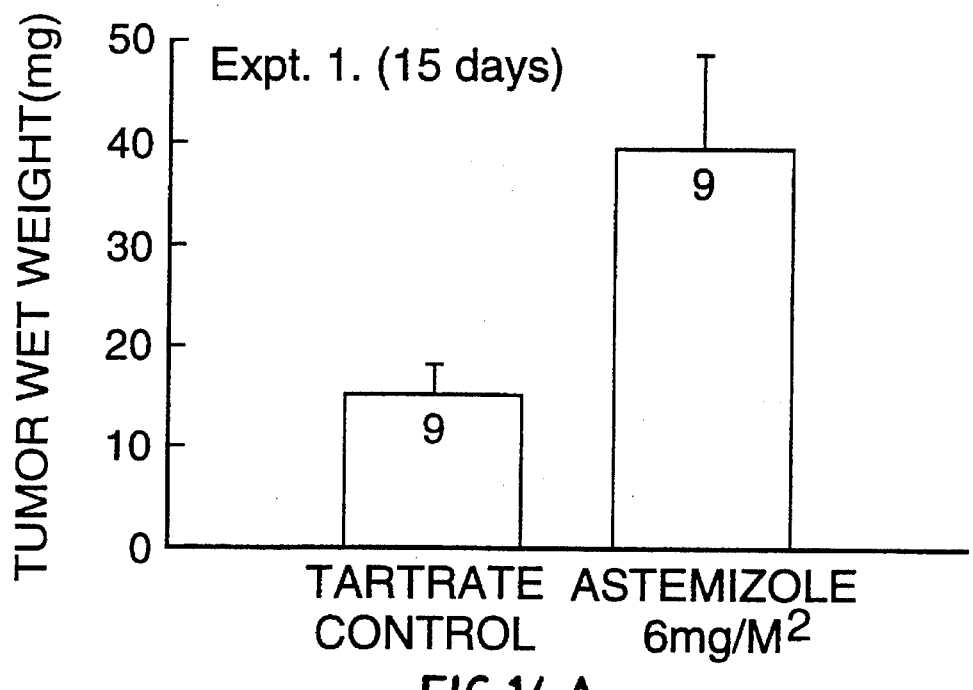
FIG.14 A.
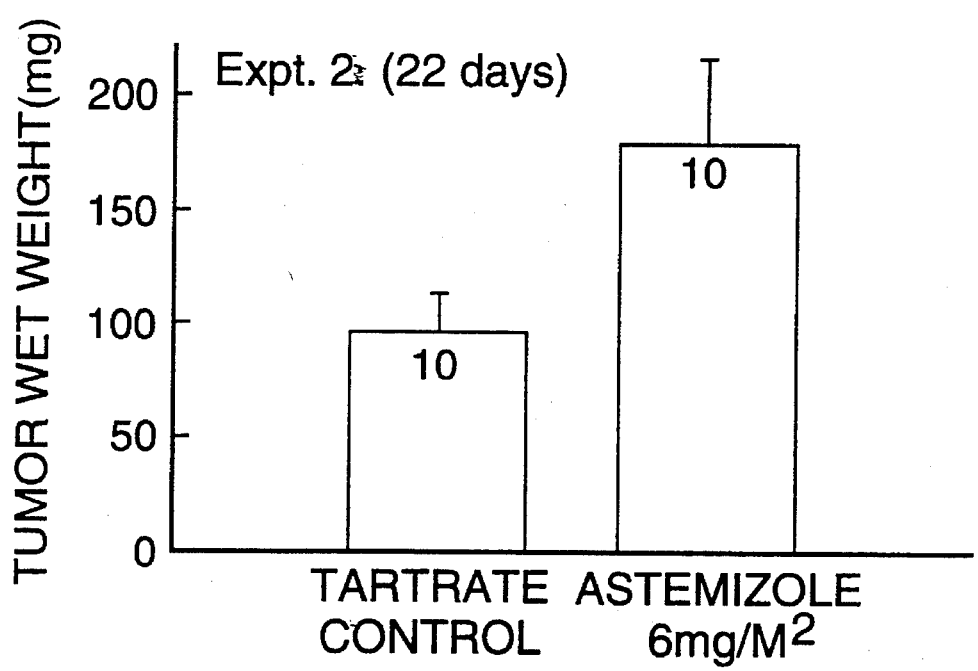
FIG.14.B.

5,618,846

TREATMENT METHOD FOR CANCER

REFERENCE TO RELATED APPLICATION

This application is a division of U.S. patent application Ser. No. 08/082,785 filed Jun. 28, 1993, which itself is a continuation-in-part of my U.S. patent application Ser. No. 711,975 filed Jun. 7, 1991, now abandoned, which itself is a continuation-in-part of U.S. patent application Ser. No. 627,863 filed Dec. 17, 1990 (now abandoned).

FIELD OF INVENTION

The present invention relates to the improved treatment of cancer in animals, including humans, using chemotherapeutic agents.

BACKGROUND TO THE INVENTION

One of the major chemotherapeutic treatments is that of malignant growth (cancer) in humans. The objective of chemotherapy is the total extermination of clonogenic tumor or malignant cells, with minimal damage to the patient. However, one of the major limitations of the chemotherapeutic approach for managing human cancer is the general inability of anticancer drugs to discriminate between normal and tumorous cells. Anti-neoplastic agents have the lowest therapeutic indicies of any class of drugs used in humans and hence produce significant and potentially life-threatening toxicities. Certain commonly-used anti-neoplastic agents have unique and acute toxicities for specific tissues. For example, the vinca alkaloids possess significant toxicity for nervous tissues, while adriamycin has specific toxicity for heart tissue and bleomycin has for lung tissue. In general, almost all members of the major categories of anti-neoplastic agents have considerable toxicities for normal cells of gastrointestinal, epidermal and myelopoietic tissues.

Generally, the dose-limiting consideration for chemical management of cancer in humans is the toxicity that anti-neoplastic agents have for the pluripotent stem cells of myelopoietic tissue. This toxicity arises from the fact that most anticancer drugs function preferentially against proliferating cells but with no significant capacity to discriminate between cycling normal and cycling tumor tissues.

Attempts have been made to confer specificity upon presently-available chemotherapeutic agents. In Anticancer Research 6:451 to 464 (1986), Robert C. Warrington describes certain in vitro and in vivo experiments demonstrating the achievement of improvements in both the specificity and efficacy of a number of commonly-used anticancer drugs by using these agents in combination with L-histidinol. L-histidinol is a structural analogue of the essential amino acid, histidine, in which the α-carboxyl group has been reduced to a primary alcohol, and is a precursor of histamine. In the work presented by Warrington in this paper, L-histidinol was found in mice to be effective at doses of approximately 1000 mg/kg (4000 mg/M$^2$) of tissue administered five hours or more prior to the chemotherapeutic agent.

SUMMARY OF INVENTION

It now surprisingly has been found that, if a potent antagonist selective for a recently-discovered intracellular histamine receptor, designated $H_{IC}$, different from traditional histamine receptors classified as $H_1$, $H_2$ or $H_3$, is administered to a living animal having cancer, then the specificity and efficacy of chemotherapeutic agents for cancer cells is improved. By employing a potent and selective antagonist to inhibit the binding of intracellular histamine, the improved effect is obtained at significantly lower dosage levels administered for a significantly shorter period of time prior to administration of the chemotherapeutic agent than is shown in the Warrington work referred to above.

The present invention is broadly applicable to the treatment of malignant cells in a living animal where the administration of chemotherapeutic agents normally adversely affects the normal (i.e. non-malignant) cells in the animal. By first administering to the animal a potent antagonist selective for intracellular histamine receptors in an amount sufficient to inhibit binding of intracellular histamine in normal cells at the intracellular histamine binding site, the specificity and efficacy of subsequently administered therapeutic agents on malignant cell is improved.

Accordingly, in one aspect of the present invention, there is provided a method for the treatment of cancer cells in a living animal, which comprises (a) administering to the animal a potent antagonist selective for intracellular histamine receptors in an amount sufficient to inhibit the binding of intracellular histamine in normal and malignant cells, and (b) subsequently administering to the animal at least one chemotherapeutic agent in an amount toxic for the cancer cells, whereby an enhanced toxic effect on the cancer cells from the at least one chemotherapeutic agent is obtained while, depending on the dose of the intracellular histamine antagonist, adverse effects of the at least one chemotherapeutic agent on normal cells, particularly bone-marrow or gastro-intestinal cells is significantly ameliorated.

It has further been found that, if a patient being treated with a chemotherapeutic agent also is given an IV infusion of a low dose of a potent antagonist selective for intracellular histamine receptors over a period of from about 6 to about 72 hours after administration of the chemotherapeutic agent, then the gastro-intestinal side effects generally associated with chemotherapy, namely nausea, vomiting, anorexia and stomatitis, are at least ameliorated and often prevented.

Accordingly, in another aspect of the present invention, there is provided a method for the treatment of cancer cells, which comprises (a) administering to the animal at least one chemotherapeutic agent in an amount toxic for the cancer cells, and (b) administering to the animal for a period of up to about seventy-two hours a potent antagonist selective for intracellular histamine receptors in an amount sufficient to inhibit the binding of intracellular histamine in normal cells, whereby the side effects of administration of the chemotherapeutic agent are at least ameliorated.

In the application of the present invention to human beings, the materials generally are administered by intravenous infusion. In one preferred procedure, a solution of the potent antagonist is administered to the patient over the desired period of time prior to administration of the chemotherapeutic agent, a solution of the chemotherapeutic agent in combination with the potent antagonist then is administered for the period of time of administration of the chemotherapeutic agent, and a solution of the potent antagonist thereafter is administered to the patient for the desired period to ameliorate side effects from the chemotherapeutic agent administration.

BRIEF DESCRIPTION OF DRAWINGS

FIGS. 1 to 14 are graphical representations of test data generated in certain experiments set forth in the Examples below.

GENERAL DESCRIPTION OF INVENTION

Figure 1:
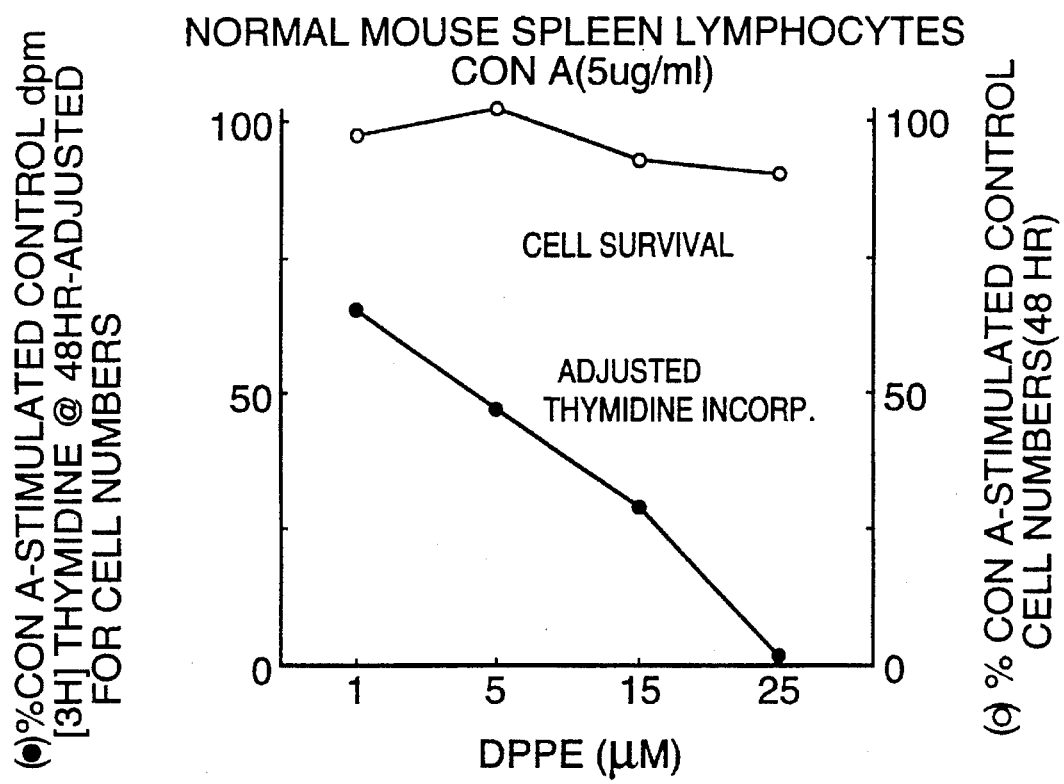

In the present invention, any compound which is a potent antagonist of histamine binding at the intracellular histamine receptor is useful and is administered in an amount sufficient to inhibit the binding of intracellular histamine at the intracellular binding site ($H_{IC}$) in normal cells. Such compounds generally exhibit a pKi of at least about 5, preferably at least about 5.5.

Specific potent compounds which are useful in the present invention are diphenyl compounds of the formula:

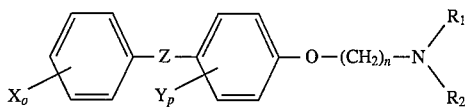

wherein X and Y are each fluorine, chlorine or bromine, Z is an alkylene group of 1 to 3 carbon atoms or C=O, and p are 0 or 1, $R_1$ and $R_2$ are each alkyl groups containing 1 to 3 carbon atoms or are joined together to form a hetero-ring with the nitrogen atom and n is 1, 2 or 3. Pharmaceutically-acceptable salts of the diphenyl compounds may be employed.

Alternatively, the benzene rings may be joined to form a tricyclic ring, in accordance with the structure:

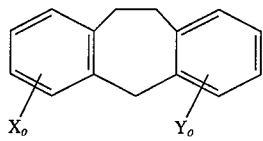

In one preferred embodiment, the group

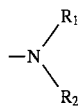

is a diethylamino group, although other alkylamino groups may be employed, such as dimethylamino, and, in another preferred embodiment, a morpholino group, although other heterocyclic ring groups may be employed, such as piperazino. o and p are usually 0 when Z is an alkylene group and n may be 2. In one particularly preferred embodiment, Z is —CH$_2$—, n is 2, o and p are each 0 and

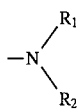

is a diethylamino group. This compound, namely N,N-diethyl-2-[4-(phenylmethyl)-phenoxy]ethanamine, in the form of its hydrochloride salt, is abbreviated herein as DPPE. In addition to a methyl group linking the benzene rings, other linking groups may be employed, such as =C=O. Other substitutions may be made on the benzene rings in addition to the halogen atoms, for example, an imidazole group.

The compounds used herein are potent antagonists of intracellular histamine binding at a site designated $H_{IC}$. Such compounds, in an intracellular histamine binding assay, generally exhibit pki values of at least about 5, preferably at least about 5.5. For example, DPPE exhibits a pki value of 6.5. L-histidinol used in the Warrington work referred to above, is not as selective for intracellular histamine receptors and in this regard, possesses a pki value of 3.1. Although weak affinity for binding to $H_{IC}$ is exhibited by L-histidinol, this compound binds more strongly to other histamine binding sites, including $H_2$ and $H_3$. The present invention employs compounds which potently and preferentially bind to $H_{IC}$.

In the present invention, significantly-smaller quantities of the antagonist compound are used in humans when compared to L-histidinol (typically 6 mg/kg or 240 mg/M$^2$ vs. 1000 mg/kg or 4000 mg/M$^2$) and the antagonist compound is administered in the present invention over a much shorter period before the chemotherapeutic agent(s) when compared to L-histidinol (typically 60 minutes vs. 5 hours).

The antagonist compound employed in the present invention is administered to the patient in any convenient manner, such as by intravenous injection of a solution thereof in an aqueous pharmaceutically-acceptable vehicle.

The antagonist compound is administered to the patient over a suitable period of time before administration of at least one chemotherapeutic agent. The chemotherapeutic agent or a mixture of such agents may be administered in any convenient manner consistent with its normal manner of administration following conventional chemotherapeutic practice, often by intravenous infusion of a solution thereof. Such chemotherapeutic agent solution may also contain the antagonist compound. The invention is widely applicable to any type of known anti-cancer drug, which tend to be compounds specific for treatment of one type of cancer. A number of specific examples of such anti-cancer drugs appear in the illustrated experimental data below.

The administration of the antagonist compound to the patient prior to administration of the chemotherapeutic agent is necessary in order to permit the antagonist to inhibit the binding of intracellular histamine in normal and malignant cells and thereby, in effect, shut down proliferation of the normal cells, but increase proliferation of malignant cells.

The length of time prior to administration of the chemotherapeutic agent that the antagonist compound is administered depends on the antagonist compound, its mode of administration and the size of the patient. Generally, the antagonist compound is administered to the patient for about 30 to about 90 minutes, preferably about 60 minutes, prior to administration of the at least one chemotherapeutic agent.

The quantity of antagonist compound administered to the patient depends on the side effects to be ameliorated, but should be at least sufficient to inhibit binding of intracellular histamine in normal cells. The quantity required to achieve the beneficial effects of the present invention depends upon the antagonist compound employed, the chemotherapeutic agent employed and the quantity of such agent employed.

In general, the quantity of antagonist compound employed in humans is from about 8 to about 320 mg/M$^2$ of animal to which the antagonist compound is administered, with about 8 and 240 mg/M$^2$ being the optimal dose for gastro-intestinal and bone marrow protection, respectively. Over this dose range, the present invention is able to achieve an enhanced chemotherapeutic effect on cancer cells while, at the same time, also protecting normal cells from damage by the chemotherapeutic agent in a wide variety of circumstances where traditional chemotherapy leads to damage of normal cells or tissues not involved in the disease process. Examples of the most common adverse effects on normal cells which result in traditional chemotherapy include:

(a) the killing of, or damage to, bone marrow cells, and (b) the killing of, or damage to, normal cells lining the gastrointestinal tract.

In cancer-bearing animals, DPPE treatment alone modulates tumor growth with promotion at lower doses and inhibition (cytotoxicity) at higher doses. However, when combined with known anti-cancer drugs in the manner described herein, a marked synergistic action is observed whereby tumors are inhibited or killed by the anti-cancer drugs. This effect has led, for example, to marked regressions or cures in some animal, including human, cancers, such as sarcoma and melanoma.

As noted above, continued administration of the antagonist compound following administration of the chemotherapeutic agent, specifically up to about 30 mg/M$^2$ of DPPE on a daily basis, at least ameliorates, and often eliminates, the side effects often associated with chemotherapy, including nausea, vomiting, anorexia and stomatitis, and preferably is effected herein, with the longer the period of administration, the more significant is the protection against the side effects. A daily dose of about 240 to about 1200 mg/M$^2$ of DPPE affords maximum bone marrow protection and synergy with chemotherapy to kill cancer cells.

Such continued administration of antagonist component is most conveniently effected by intravenous administration, although oral administration at the lower dose range may be feasible and, in some cases, more desirable from the standpoint of patient acceptance and of decreasing the load on the medical facility.

It has also been found that DPPE alone at low doses directly stimulates tumor cell growth in vivo and also increases the inflammatory response in skin elicited by the tumor promoting phorbol ester, PMA (phorbol myristate acetate). Several other classes of compounds, such as antidepressants, phenothiazines, triphenylethylene estrogens, histamine ($H_1$, $H_2$, $H_3$) antagonists, serotonin ($5HT_1$, $5HT_3$) antagonists, β-andrenergic antagonists and imidazole analogs, also have been identified as producing the same results as observed for DPPE.

It now also has been found that tricyclic antidepressant drugs and the non-tricyclic agent, fluoxetine (Prozac™), as well as $H_1$-antihistamine and β-adrenergic antagonists, also compete for the binding of $^3$H-DPPE and $^3$H-histamine to $H_{IC}$ in rat liver microsomes or brain membranes and, likewise, promote tumor growth.

Such compounds mimic the profiles of DPPE to inhibit normal cell proliferation but to promote malignant cell proliferation. Accordingly, these materials, at the proper dose level, could be predicted to increase the therapeutic index of chemotherapy drugs and are included within the scope of this invention.

Accordingly, in another aspect, the present invention provides a method for the treatment of cancer wherein a compound which inhibits normal cell proliferation while promoting malignant cell proliferation is combined with chemotherapy agents to increase the therapeutic index of chemotherapy drugs, in like manner to DPPE and similar potent antagonists of intracellular histamine binding as specifically described herein.

Among the various compounds which may be employed in this aspect of the present invention are included:

(a) tricyclic antidepressants, such as amitriptyline, clomipramine and imipramine, (b) non-tricyclic depressants, such as fluoxetine, (c) phenothiazines, such as prochloroperazine, trifluoroperizine and chlorpromazine, (d) $H_1$ antagonists, such as loratadine, hydroxyzine, phenyltoloxamine and astemizole, (e) β-adrenergic agonists and antagonists, such as propanolol, (f) serotonin ($5HT_1$ or $5HT_3$) antagonists, such as ondansertron ($5HT_3$) and cyproheptadine ($5HT_1$), (g) imidazoles and imidazole-like compounds, including $H_2$ antagonists, such as cimetidine and ranitidine, $H_3$ antagonists, such as thioperamide and antifungal agents, such as ketoconazole, and (h) triphenylethylene derivatives, such as tamoxifen.

In general, the compounds which may be employed in this aspect of the invention may have a chemical structure consisting of at least two phenyl rings, linked by a rigid third phenyl or non-phenyl ring, or by a non-rigid methyl, oxygen or other moiety, with the phenyl ring structure being linked by an ether, sulfhydryl or other ring structure or group to a basic alkylamine, imidazole or amino-imidazole side chain, for example, the carboxyamide-amino-imidazole L651582.

Although this wide range of compounds may be employed to increase the therapeutic index of chemotherapy drugs, DPPE and its direct analogs, may be significantly better agents for combination with chemotherapy than the foregoing groups of compounds, since DPPE appears to be more potent and selective for $H_{IC}$ and does not interact with calmodulin, protein kinase C or calcium channels and is only a weak antagonist at other common receptors, such as $H_1$, 5HT and $D_2$.

For example, DPPE does not cause serious toxic effects in humans at clinically relevant doses to enhance chemotherapy, whereas, for example, at their relevant concentrations to antagonize $H_{IC}$, the antidepressant group of drugs and histidinol may cause cardiac arrythmias, $H_1$ antagonists might cause marked sedation, heart block or convulsions and phenothiazines may cause dyskenesias.

THEORY

While the applicant does not wish to be bound by any theory to explain the beneficial effects achieved by the present invention, the following theory is proposed. The compound administered to the patient is a potent, selective antagonist of histamine binding at a newly-discovered novel intracellular receptor ($H_{IC}$) (see, for example, "Histamine as an Intracellular Messenger" by Brandes et al, Biochem. Pharmacol., vol 40, 1990, pp 1677–1681). Intracellular histamine normally functions through this receptor to mediate or modulate many important cell functions, including cell proliferation, immune responses and platelet aggregation.

Protection of the normal cells is achieved through antagonism of histamine at $H_{IC}$ by the antagonist. Such antagonism results in a temporary complete shut-down of cell division, so that normal cells are not susceptible to DNA damage in the presence of the chemotherapeutic agent(s), which preferentially attack dividing cells. In this way, for example, DPPE is effective to block therapy-associated toxicity of normal bone marrow stem cells.

In addition, the antagonism results in an increase in the levels of prostaglandins (natural substances which are known to protect tissues from various injurious agents) in the tissue. For example, DPPE treatment results in an increase by 500% in prostaglandin (PG)$I_2$, a protective prostaglandin, in the gut. Through this mechanism, DPPE is known to completely block ulcer formation in the presence of noxious agents, such as alcohol and cysteamine (see U.S. Pat. No. 4,829,068 in which I am a co-inventor).

The antagonist further effects a potent blockage of the degranulation of tissue mast cells, whose granular contents, including histamine itself, have been linked to tissue damage and severe systemic side effects. Certain anti-cancer drugs, such as adriamycin, cause significant mast cell degranulation, an effect which has been related to cardiotoxic effects.

As with bone marrow cells, the treatment of normal proliferating lymphocytes (immune cells), according to the invention, results in a dose-dependent blocking of DNA synthesis and a shut-down of these cells without causing cytotoxicity. The antagonist has an effect on both T-lymphocytes and B-lymphocytes in the immune system. For example, DPPE is able to completely antagonize proliferation of T-lymphocytes in the presence of Concanavalin A, a potent mitogen and plant lectin. DPPE also blocks the stimulation of antibody formation by the mediator interleukin-2 in certain B cells, resulting is a decrease in antibody formation.

In contrast to its cytoprotective effect on normal cells and tissue in vivo, as described herein, DPPE treatment stimulates, damages and/or kills malignant cells in vitro, depending on the dose, as described in U.S. Pat. No. 4,803,227, or those which are virally infected.

EXAMPLES

Example I

This Example illustrates in vivo augmentation by DPPE of adriamycin anti-tumor activity in a murine sarcoma model.

C-3 fibrosarcoma cells ($3\times10^5$) were injected into the left gluteal region of C3H mice on day 0. On day 1, the mice were provided with treatment by a combination of DPPE and adriamycin, administered intraperitoneally. The DPPE was administered 60 minutes prior to administration of the adriamycin. Mice also were administered with saline, DPPE alone and adriamycin alone.

Animals in the experiments (n=12 for each group) were followed for 60 days. At the end of the experimental period, those animals free of palpable tumors were considered cured.

The results obtained are set forth in the following Table I:

TABLE I

| Treatment | Number of Rats Tumor-Free (n = 12) |
| --- | --- |
| Saline | 1 |
| Adriamycin (2 mg/kg) | 0 |
| DPPE (50 mg/kg) | 0 |
| DPPE (2 mg/kg)/Adriamycin (2 mg/kg) | 1 |
| DPPE (25 mg/kg)/Adriamycin (2 mg/kg) | 3 |
| DPPE (50 mg/kg)/Adriamycin (2 mg/kg) | 7 |

It will be seen from the results set forth in the above Table I, that, when adriamycin and DPPE alone are administered, no effect was obtained whereas when increasing quantities of DPPE were employed in combination with a constant quantity of adriamycin, an increased anti-tumor activity was observed, such that, at the highest dose of DPPE tested (50 mg/kg), 7 out of the 12 animals were cured.

Example II

This Example illustrates protection of bone marrow progenitors by DPPE in mice treated with a lethal dose of 5FU and adriamycin.

Mice of the strain C57B1 were administered a lethal dose (7.5 mg) of 5FU (5-fluorouracil), DPPE (100 mg/kg) or a combination of a lethal dose of 5FU and DPPE (100 mg/kg or 4 mg/kg) and the results were compared with a control group to which saline only was administered. The DPPE and saline were administered immediately prior to the 5FU. Bone marrow cell counts were made at 24 hours and 48 hours post administration.

The results obtained are set forth in the following Table IIA:

TABLE IIA

| Treatment | CFU-C/ $10^4$ cells[1] | | R.C.S.[2] | |
| --- | --- | --- | --- | --- |
| | 24 h | 48 h | 24 h | 48 h |
| Saline | 38.3 | 40.3 | 1.0 | 1.0 |
| 5FU | 0.2 | 0.09 | 0.006 | 0.002 |
| DPPE | 36.7 | 38.6 | 0.96 | 0.96 |
| DPPE (100 mg/kg) + 5FU | 35.7 | 37.3 | 0.93 | 0.93 |
| DPPE (4 mg/kg) + 5FU | 38.3 | 33.3 | 1.0 | 0.83 |

Note:
[1] No. of bone marrow colonies. CFU-C = colony-forming units in culture
[2] Relative Cell Survival Experiments paralleling those described above with 5FU were carried out employing a lethal dose of adriamycin (20 mg/kg). The results obtained from these experiments are set forth in the following Table IIB:

TABLE IIB

| Treatment | CFU-C/ $10^4$ cells | | R.C.S. | |
| --- | --- | --- | --- | --- |
| | 24 h | 48 h | 24 h | 48 h |
| Saline | 43.7 | 42.7 | 1.0 | 1.0 |
| Adriamycin | 1.8 | 0.65 | 0.04 | 0.006 |
| DPPE (4 mg/kg) | 42.3 | 41.3 | 0.97 | 0.97 |
| DPPE (4 mg/kg)/ Adriamycin | 39.7 | 39.0 | 0.91 | 0.91 |
| DPPE (100 mg/kg)/ Adriamycin | 43.3 | 41.3 | 0.99 | 0.97 |

As may be seen from the results set forth in the above Tables IIA and IIB, the administration of the DPPE along with the 5FU or adriamycin provided almost complete protection for bone marrow progenitors from the lethal effects of the 5FU or adriamycin.

Example III

This Example illustrates in vivo augmentation of BCNU anti-tumor activity in a B16 melanoma lung metastasis model.

$5\times10^4$ B16 melanoma cells were injected intravenously into the tail vein of C57B1 mice at day 0. The mice were treated with either saline, 32 mg/kg of DPPE, 1 mg of BCNU or a combination of 32 mg/kg of DPPE and 1 mg of BCNU, by intraperitoneal injection on day 1. The DPPE was administered 60 minutes before the BCNU.

In each group, six of the twelve animals were sacrificed at day 14 and lungs were removed for determination of metastasis. The remaining six animals were followed to death. The numbers and size of the lung metastases were determined by visual or microscope count.

The results obtained are set forth in the following Table III:

TABLE III

| Treatment | Numbers and (% control) of lung metastases | | Size of lung metastases (1) | Median Survival (days) |
|---|---|---|---|---|
| Saline | 241 | — | All Macro | 19 |
| DPPE | 219 | (91%) | All Macro | 21 |
| BCNU | 144 | (60%) | All Macro | 24 |
| DPPE/BCNU | 58 | (27%) | All Micro | 32 |

(1) Macro means visually determined. Micro means microscopically only.

As may be seen from the results in Table III, the inhibitory effect of BCNU on the lung tumors was significantly increased by the additional presence of DPPE, which itself alone had a marginal effect.

Example IV

This Example illustrates in vivo augmentation of daunorubicin anti-tumor activity in a B16 melanoma lung metastasis model.

The procedure of Example III was repeated employing daunorubicin in place of BCNU. Groups of six mice were injected with B16f10 melanoma cells and 24 hours later received saline, 4 mg/kg of DPPE alone, a non-lethal dose of daunorubicin alone (12.5 mg/kg) or DPPE (4, 25 or 50 mg/kg) one hour prior to daunorubicin (12.5 mg/kg). All animals were followed to death or for 60-days post injection, and sacrificed for lung metastases.

The results obtained are set forth in the following Table IV:

TABLE IV

| Treatment Group | Median-Survival (days) | No. Cures (n = 6) |
|---|---|---|
| Saline | 17 | 0 |
| Daunorubicin (12.5 mg/kg) | 25 | 0 |
| DPPE (4 mg/kg) + Daunorubicin (12.5 mg/kg) | 29 | 2 |
| DPPE (25 mg/kg) + Daunorubicin (12.5 mg/kg) | 60+ | 4 |
| DPPE (50 mg/kg) + Daunorubicin (12.5 mg/kg) | 60+ | 4 |

As may be seen from the results of Table IV, the inhibitory effect of daunorubicin or lung tumors was enhanced by the presence of DPPE.

Example V

This Example shows in vivo host cytoprotection from a lethal dose of adriamycin.

Saline or DPPE (2 mg/kg) were administered to DBA/2 mice 1 hour (n=12) or 15 minutes (n=6) prior to administration of 15 mg/kg of adriamycin. The number of survivors after 30 days was determined. The results are set forth in the following Table V:

TABLE V

| Treatment | Number of Survivors |
|---|---|
| Saline | 4/12 (33%) |
| DPPE | 13/18 (72%) |

As may be seen from Table V, the administration of DPPE provided in vivo host cytoprotection from the lethal dose of adriamycin.

Example VI

This Example illustrates the effect of DPPE on thymidine incorporation into lymphocyte DNA.

Spleen cells from BALB/C mice were stimulated with Concanavalin A (5 µg/ml). The cells then were treated with varying does of DPPE and the level of thymidine incorporated into DNA was determined. The results were plotted graphically and appear as FIG. 1. As may be seen from this Figure, at a dosage level of 25 µM, DPPE completely blocks thymidine incorporation into DNA but does not adversely affect cell survival. Thus, the DPPE treatment puts normal proliferating lymphocytes into a state of growth arrest without causing cytotoxicity.

Figure 2:
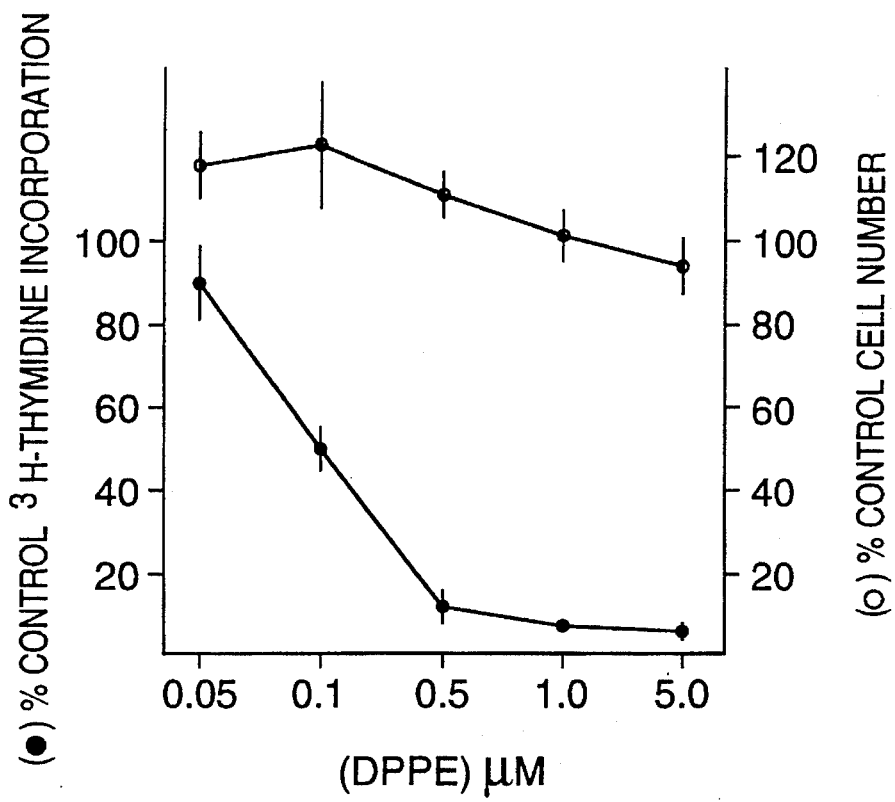

The experiment was repeated using 2.5 µg/ml of Concanavalin A in place of 5 µg/ml and 2% fetal calf serum in place of 10%. The results obtained are illustrated in FIG. 2. At concentrations of DPPE which inhibited DNA synthesis (5 µm), no significant cytotoxicity was observed.

Example VII

This Example illustrates the effect of DPPE on thymidine incorporation into DNA in transformed lymphocytes.

Figure 3:
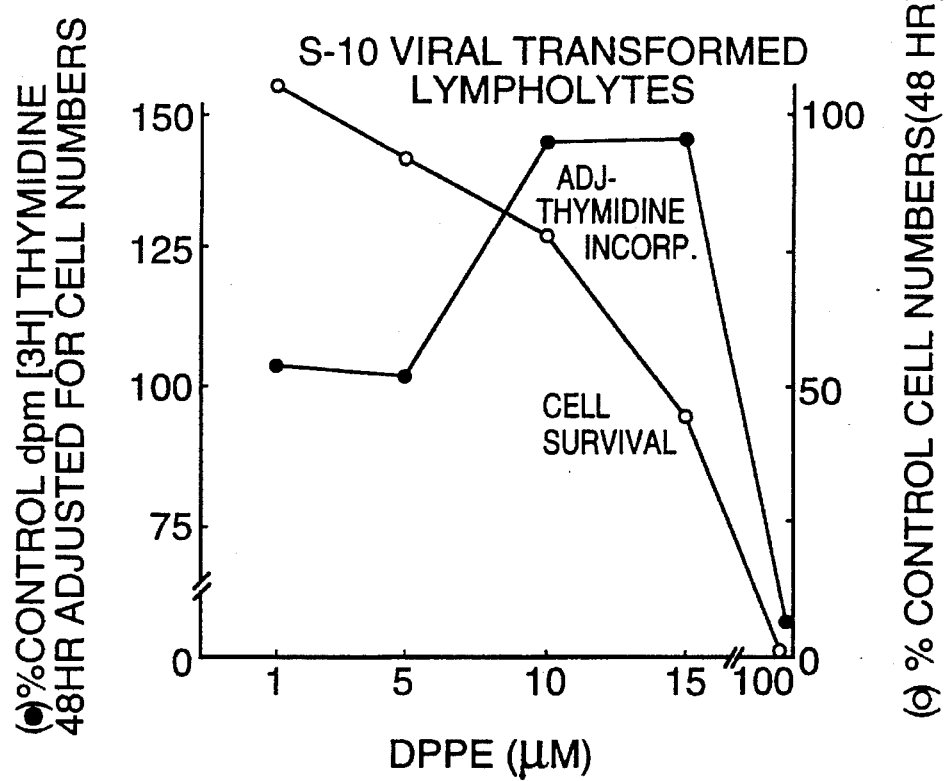
Figure 4:
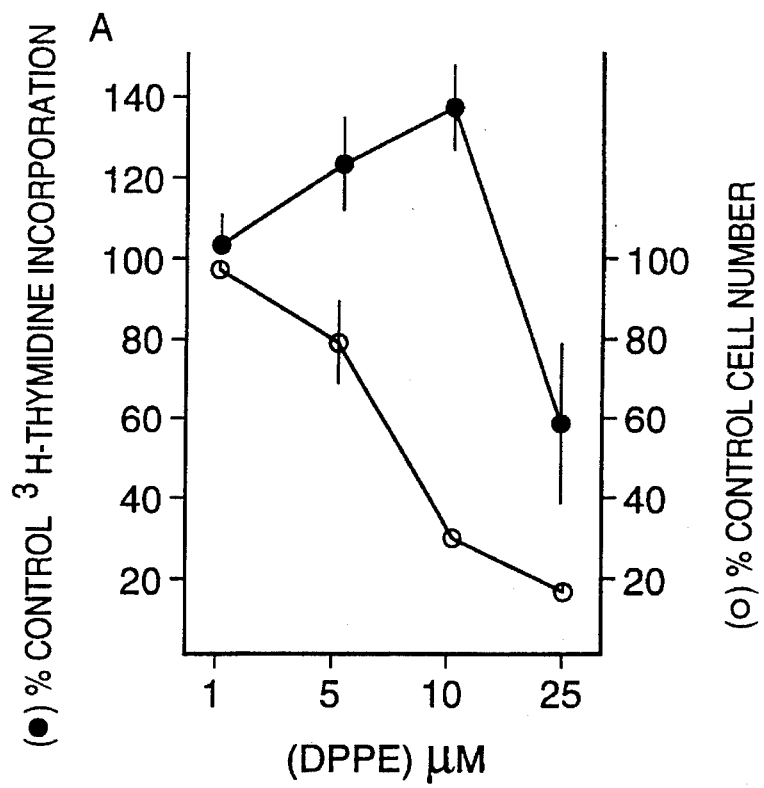

The experiment of Example VI was repeated employing virally-infected non-senescing transformed spleen-derived lymphocytes (S-10) also of BALB/C origin with 0.25 nM of $^3$H-thymidine added. The results were plotted graphically and appear as FIGS. 3 and 4 respectively. As may be see therein, in contrast to FIGS. 1 and 2, 25 µM of DPPE caused approximately 50% cytotoxicity to the virally-infected cells. When adjusted for cell number, thymidine incorporation increased at cytotoxic concentrations of DPPE (10 to 25 µM).

Figure 5:
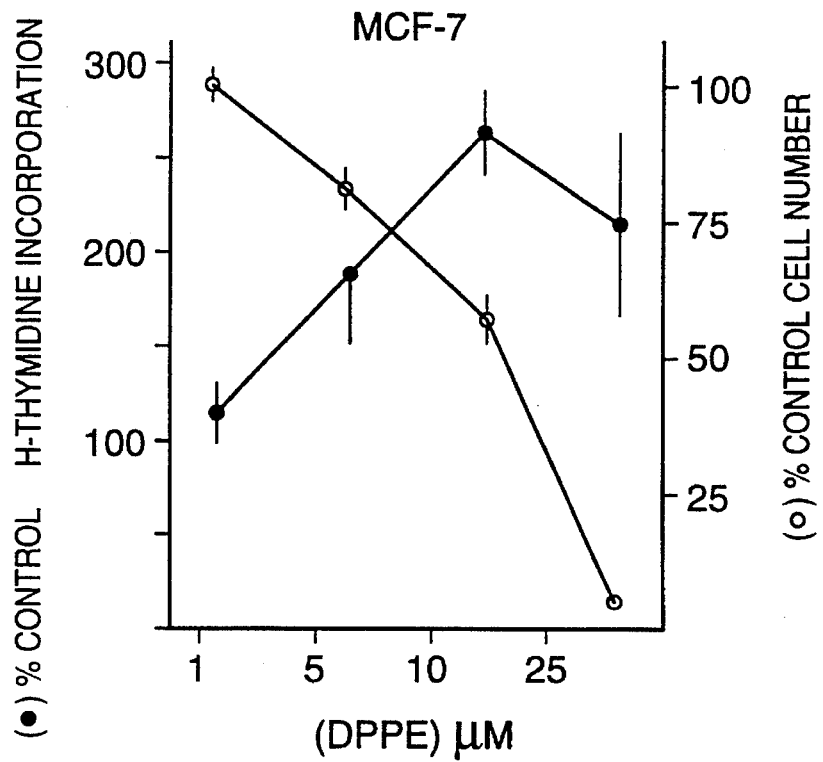

The experiment was again repeated using human breast cancer cell (MCF-7) with 0.25 nM of thymidine added. The results were plotted graphically and appear as FIG. 5. Analogous results can be seen to those observed with the S-10 cells.

Example VIII

A clinical study was carried out in 24 patients with advanced cancer.

(a) DPPE alone was administered to patients to determine a safe dose range in humans. The highest non-toxic dosage was found to be 4 mg/kg (160 mg/M$^2$) given intravenously over a one-hour period. At 6 mg/kg (240 mg/M$^2$) over one hour, CNS toxicity (as manifested by any or all of muscle twitching, a drop of 1° to 2° C. in body core temperature, auditory hyperacusis or hallucination, choreoathetosis, cerebellar ataxia and projectile vomiting) was observed. However, significant CNS toxicity was absent when 6 mg/kg (240 mg/M$^2$) was administered IV over 2 hours, suggesting that peak serum level determines CNS toxicity. When the dose is converted to mg/M$^2$, threshold for CNS toxicity occurs at the same dose previously observed in preclinical toxicology (ip route) studies in mice (240 mg/M$^2$).

(b) DPPE at a daily dose of 0.2 mg/kg (8 mg/M$^2$), given as an IV infusion over 24 to 72 hours was found to be entirely without clinical side effects, with the possible exception of constipation in occasional patients, and not to cause any significant changes in biochemistries or blood counts. This dose of DPPE also has been determined to potently prevent, or ameliorate by over 90%, nausea, vomiting, anorexia and stomatitis in 58 patient treatments with Adriamycin (60 mg/M$^2$). GI protection was most pronounced when DPPE was given at a dose of 0.2 mg/kg (8 mg/M$^2$) daily for 72 hours post-treatment by IV infusion.

(c) Higher single IV doses of DPPE (1, 2, 4 mg/kg) given over 1 hour also appear to be significantly antiemetic against Adriamycin, although some patients experienced nausea, or transient anorexia, at 4 mg/kg (160 mg/M$^2$) of DPPE alone. At doses of 1 to 6 mg/kg IV over 1 hour, DPPE alone also was found to cause a transient decrease (20 to 30%) in neutrophil counts in 4/6 patients, with complete recovery by day 5 to 7. No significant effect of DPPE alone on platelets, hemoglobin or biochemistry has been observed.

(d) Using 0.2 mg/kg (8 mg/M$^2$) of DPPE as a total daily dose, increased duration of treatment improved the therapeutic benefit to prevent nausea, vomiting, anorexia and a drop in nadir white counts, but not alopecia, caused by Adriamycin at a dosage level of 60 mg/M$^2$. A 24-hour DPPE infusion was an effective anti-emetic therapy in the first 24 to 48 hours following Adriamycin administration, but many patients then experienced delayed nausea, vomiting and/or anorexia at 72 or 96 hours after Adriamycin administration. However, when given as a 72-hour infusion, DPPE was observed to block completely all acute and delayed gastrointestinal side effects of Adriamycin in four patients. In addition, two additional patients experienced only one minor episode of nausea and/or vomiting in the first 24 hours following Adriamycin administration, but then were well without any need for antiemetics. The 72-hour infusion of low dose DPPE also prevented mouth ulceration in one patient who had previously experienced this symptom during all previous non-Adriamycin chemotherapy and DPPE/Adriamycin given in shorter schedules.

(e) As compared to other regimens of DPPE/Adriamycin, nadir polymorphonuclear WBC counts at 14 days appear to be highest in patients who received 0.2 mg/kg (8 mg/M$^2$) DPPE for 72 hours (1,285±385; mean±S.E.M.). Platelet counts have been uniformly above 150,000/mm$^3$ at Day 14.

(f) In seventeen evaluable patients, seven major responses, including three breast cancers, one lymphoma, one rhabdomyosarerma and one medullary carcinoma of thyroid, have been documented.

Example IX

In a second human pilot study, the infusion of higher doses of DPPE (2 to 12 mg/kg; optimal dose=6 mg/kg (240 mg/M$^2$)) over a period of 60 minutes prior to the administration of an antineoplastic drug resulted in significant palliation in 16/20 evaluable patients with progressive metastatic cancer, refractory to chemotherapy alone (1 complete and 6 partial remissions, 5 improved, 4 stabilized, 4 progressed). Many patients remaining on treatment (the longest for 11+ months) continue to improve, or be stable, suggesting a durable response, and that additional complete or partial remissions may result in some of these subjects.

The most impressive responses have been observed in patients with breast and colon cancer, and lymphoma. Treatment with DPPE (240 mg/M$^2$) plus 5-fluorouracil (750 mg/M$^2$) once weekly in 6 patients with breast cancer has resulted in resolution of liver metastases in two patients, progressive healing of bone metastases in one patient and significant resolution of chest wall metastases in two patients. Similarly, four patients on DPPE plus 5-FU for colon cancer with liver metastases, previously unresponsive to 5-FU plus leucovorin, have shown significant improvement of liver lesions and/or liver function and other disease-associated symptoms such as pain; a fifth patient with tumor invading the bladder, has had resolution for the past four months of gross daily hematuria. Protection of bone marrow stem cells has been observed in several patients treated with DPPE and high doses of cyclophosphamide (1 g/M$^2$). Thus, as in pre-clinical studies in mice, high doses of DPPE maximally synergize with chemotherapy to kill cancer cells, while significantly protecting the bone marrow from the myelosuppressive effects of chemotherapy.

Example X

This Example illustrates the tumor promoting and pro-inflammatory response effects of DPPE alone.

Figure 6:
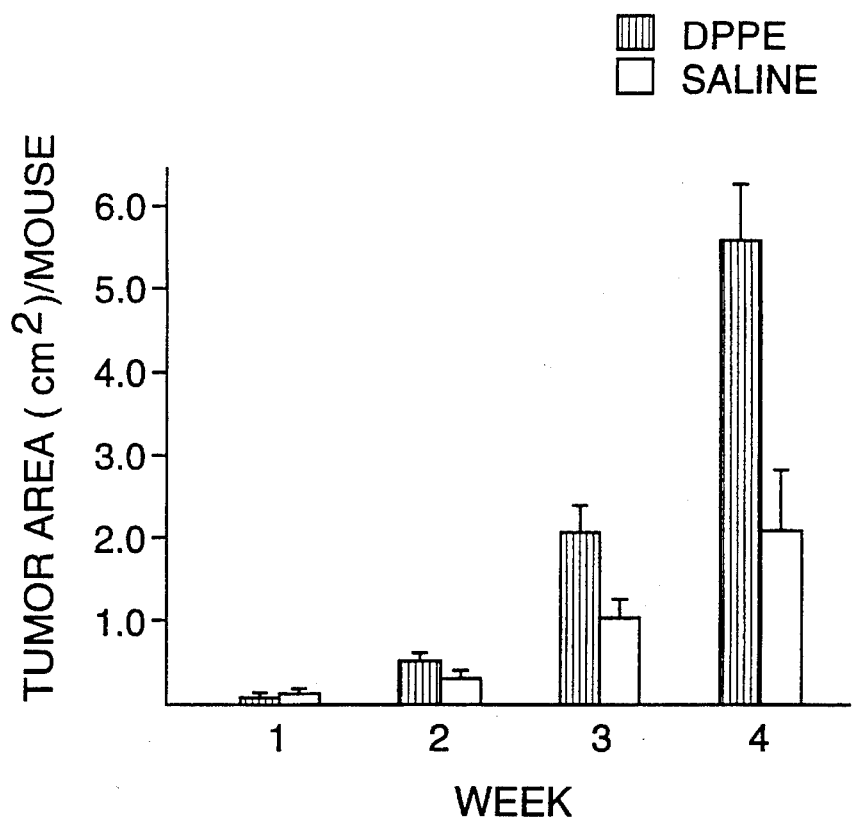

FIG. 6 shows the tumor-promoting effect DPPE (1 mg/kg or 4 mg/M$^2$) given subcutaneously once daily×3, to seven DBA/2 mice inoculated subcutaneously with 2×10$^2$ L5178Y lymphoma cells 48 hours previously. A second group of 7 tumor cell-inoculated mice served as controls (saline injections, once daily×3). By day 14, 7/7 DPPE treated animals had palpable tumors as compared to 4/7 controls. At the end of 4 weeks, 6/7 controls had tumors with an aggregate surface area of 14.5 cm$^2$ (mean=2.1±0.8 cm$^2$/animal), while 7/7 DPPE-treated animals had tumors with an aggregate surface area of 38.4 cm$^2$ (mean=5.5±0.7 cm$^2$/animal). Thus, the tumor burden of DPPE-treated animals was approximately 2.5-fold greater than that of controls.

To investigate any effect of DPPE to increase PMA-induced inflammation in the same strain of mice (DBA/2), groups of 3 animals were shaved over the back and 48 hours later received a single topical application of 17 nM PMA in acetone. The PMA-treated mice then received either saline (control) or DPPE (4 or 32 mg/kg at time 0 and 24 hours). Three animals painted with acetone served as vehicle controls. Forty-eight hours later, the various groups were sacrificed by CO$_2$ asphyxiation, the skin carefully excised, pinned to paper strips to prevent wrinkling, and immersed in formaldehyde. H and E-stained sections of skin were assessed for degree of inflammation.

It was observed that the animals who received DPPE had a significantly greater inflammatory response to PMA as compared to saline or acetone controls. The most intense inflammatory response was seen in animals receiving the high dose (32 mg/kg or 128 mg/M$^2$) of DPPE, where increased mitotic activity in the epithelial layer was also noted as compared to the PMA and saline-treated groups. The results of the experiments reported in this Example clearly show that DPPE enhances the inflammatory response of the tumor promoter PMA. Indeed, since tumor promotion requires the presence of inflammatory response, and can be blocked by agents which inhibit inflammation by definition, DPPE functions as a co-promoter with PMA.

Example XI

This Example shows the H$_{IC}$ binding and tumor promoting effects of certain compounds and the antiproliferative effect of DPPE and certain compounds.

Figure 7:
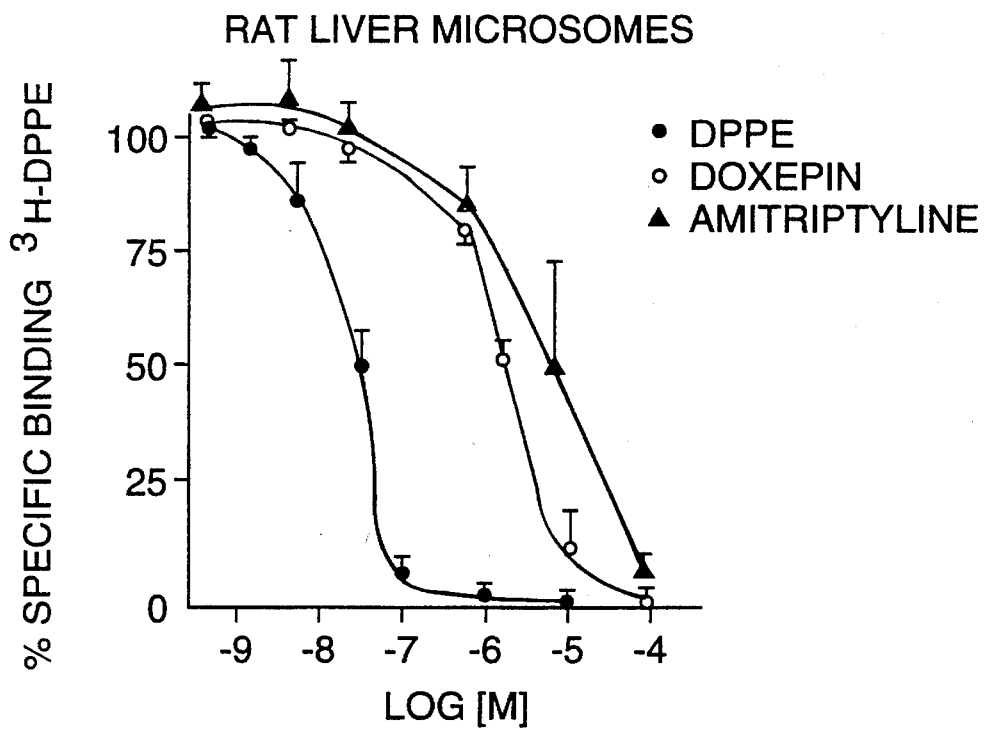
Figure 8:
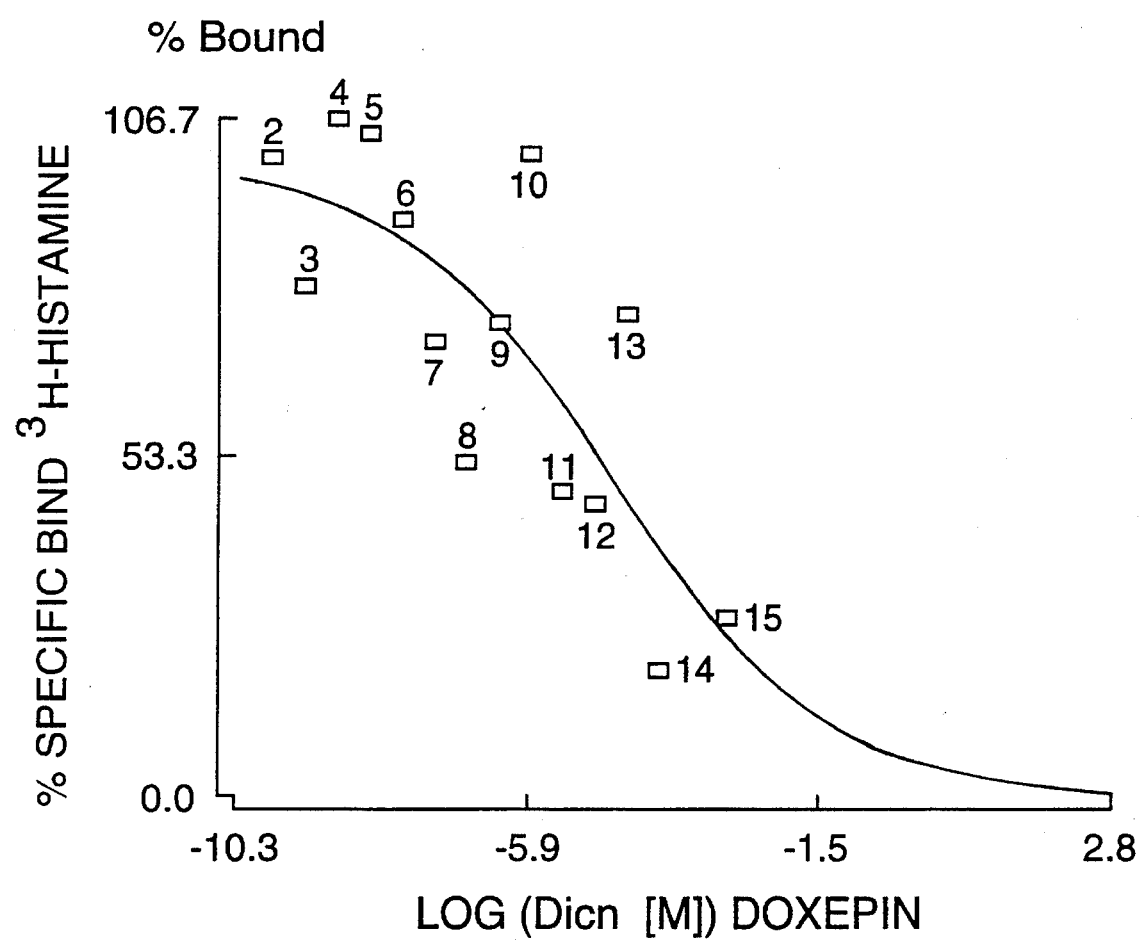

FIG. 7 shows the potency of two tricyclic agents, namely amitriptyline and doxepin, to compete for $^3$H-DPPE binding in liver microsomes. The K$_d$ value for DPPE is 65 nM while the K$_i$ for doxepin is 5 µM and for amitriptyline is 10 µM. Doxepin and fluoxetine also compete for $^3$H-histamine binding to H$_{IC}$ in brain membranes (K$_i$=10 µM; FIG. 8).

Figure 9A:
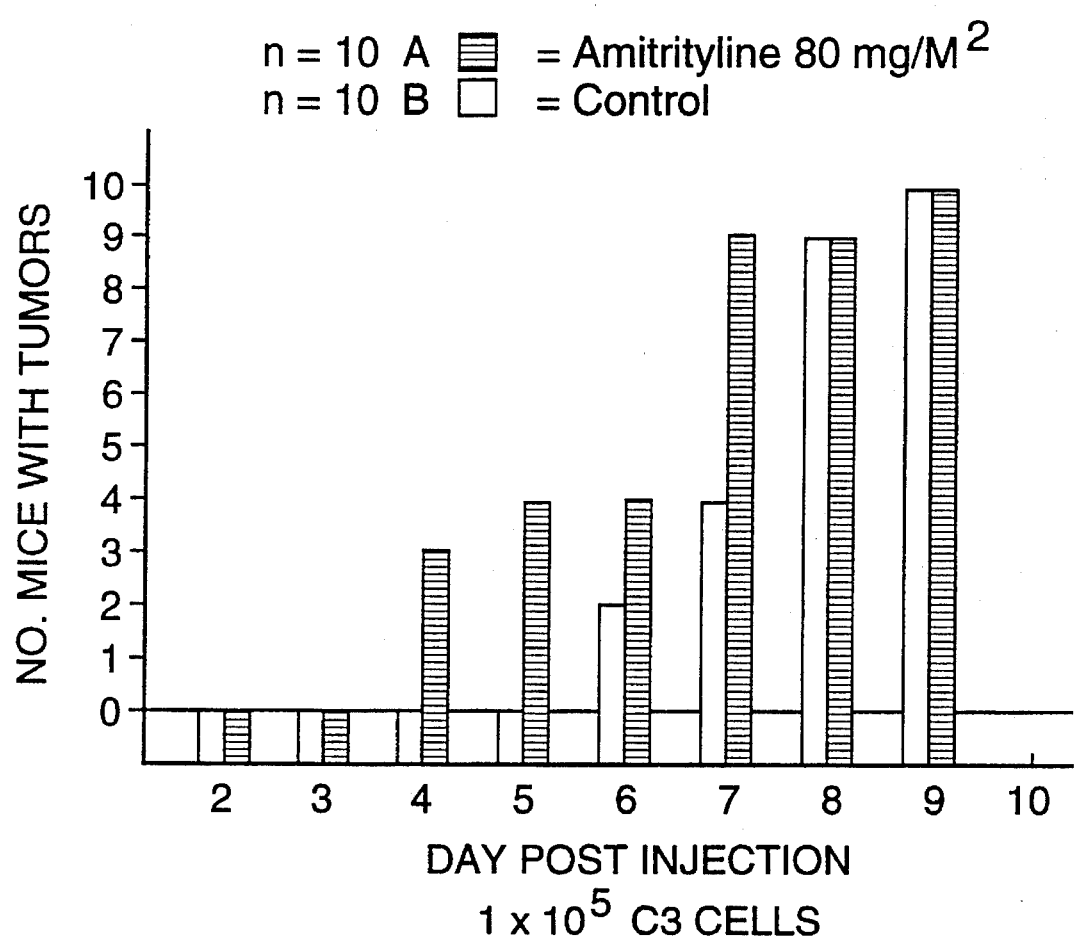
Figure 9B:
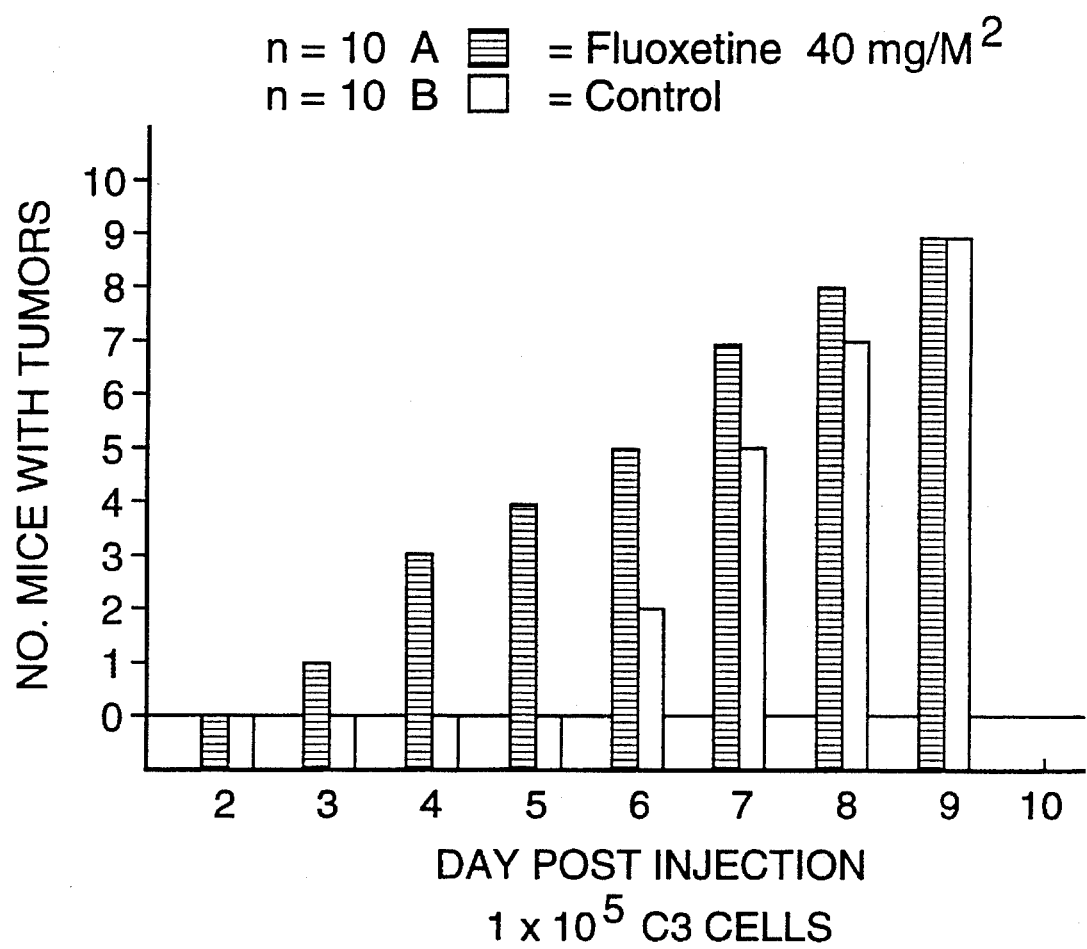

FIG. 9 demonstrates the tumor-promoting effects of the tricyclic agent, amitriptyline, and the non-tricyclic agent, fluoxetine, in C3H mice injected subcutaneously into the gluteal region with $1 \times 10^5$ C-3 fibrosarcoma cells. The doses employed were equivalent to therapeutic human doses (80 mg/M$^2$ for amitriptyline and 20–40 mg/M$^2$ for fluoxetine). The experiments were blinded so that the individual measuring the first appearance of palpable tumor was unaware of the treatment group (saline control vs antidepressant drug; n=10 in each group).

It may be seen from this data that, in both experiments, the control animals did not develop tumors until day 6, whereas in the fluoxetine-treated animals, tumors appeared on days 3, 4 and 5 post-injection and, in the amitriptyline-treated animals, tumors appeared on days 4 and 5 post-injection. Thus, in both experiments, 4/10 of antidepressant-treated animals, but no controls had tumors by day 5 (8/20 vs 0/20 controls, both experiments combined).

Figure 10:
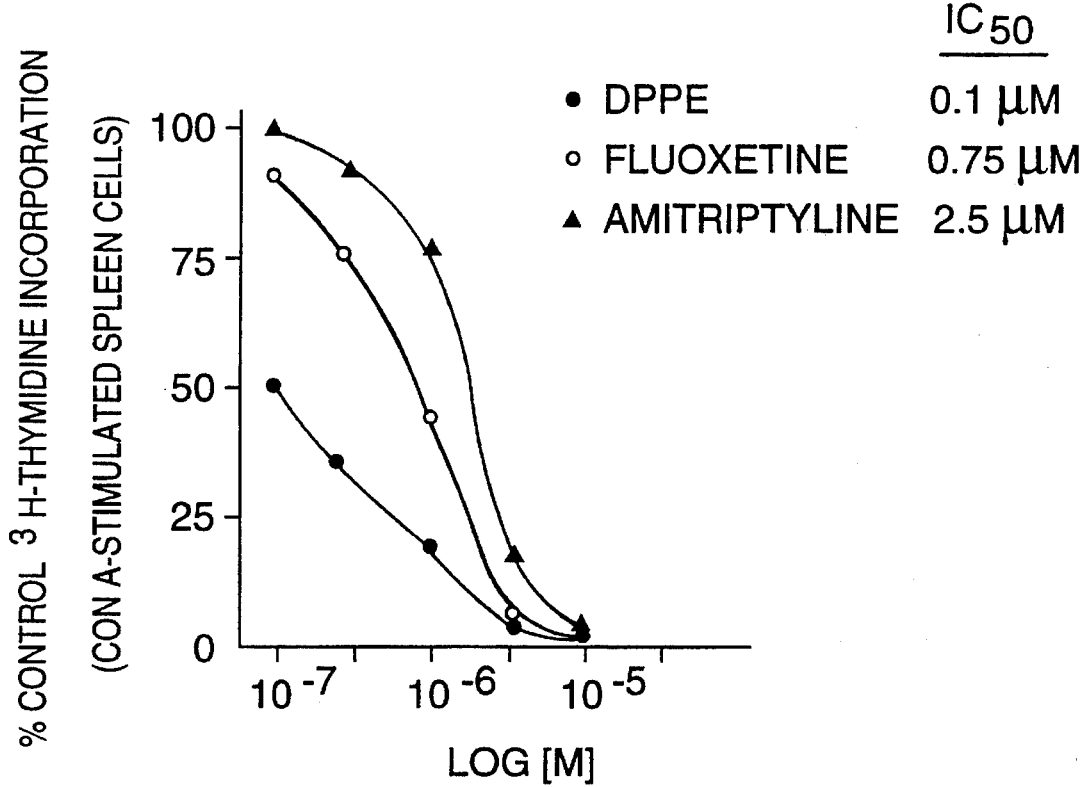

Conversely, FIG. 10 shows that, like DPPE, both amitriptyline and fluoxetine inhibit, in the absence of cytotoxicity, the proliferation of concanavalin A-stimulated normal lymphocytes (IC$_{50}$=10 to 20 μM). Thus, although weaker than DPPE, these agents inhibit the proliferation of normal stem cells while increasing the proliferation of tumor cells.

Figure 11:
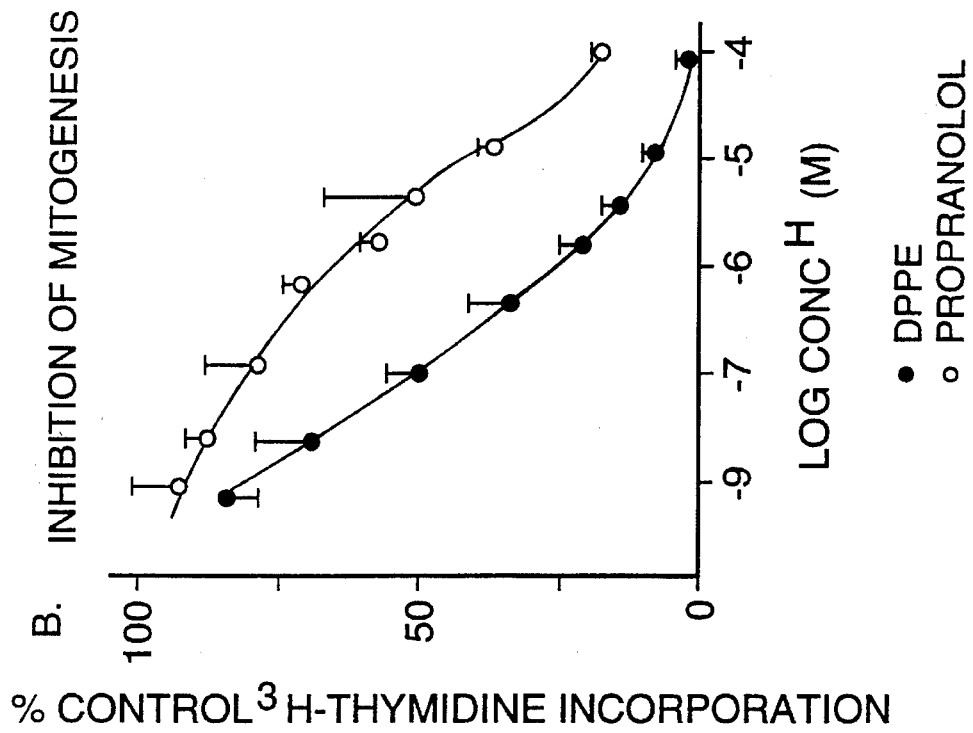
Figure 11A:
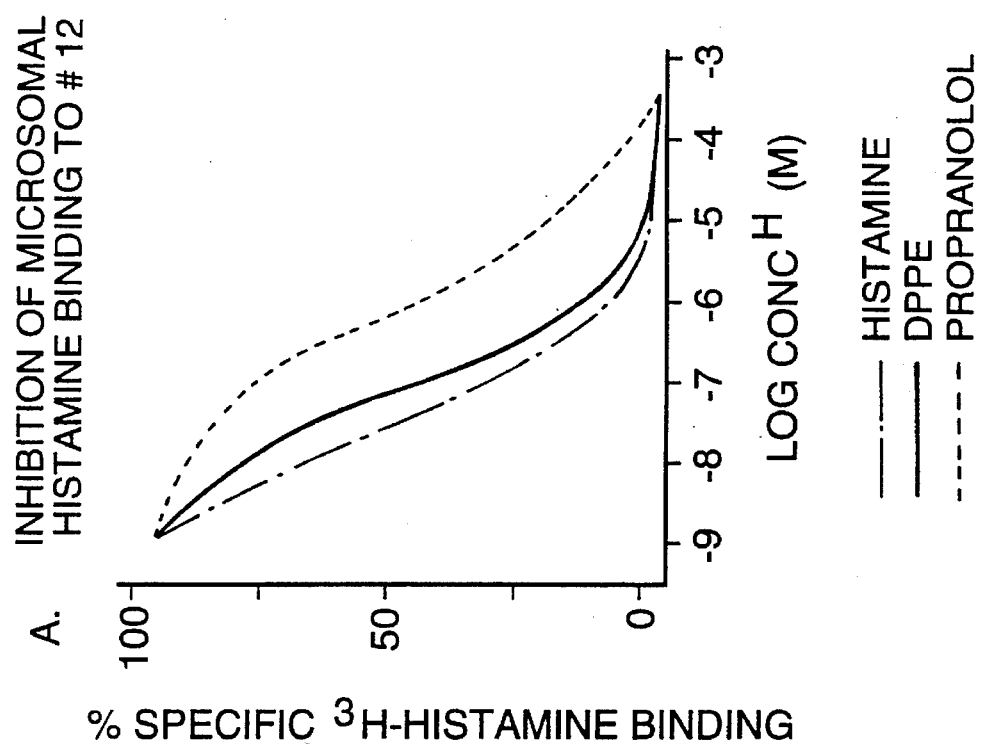
Figure 12:
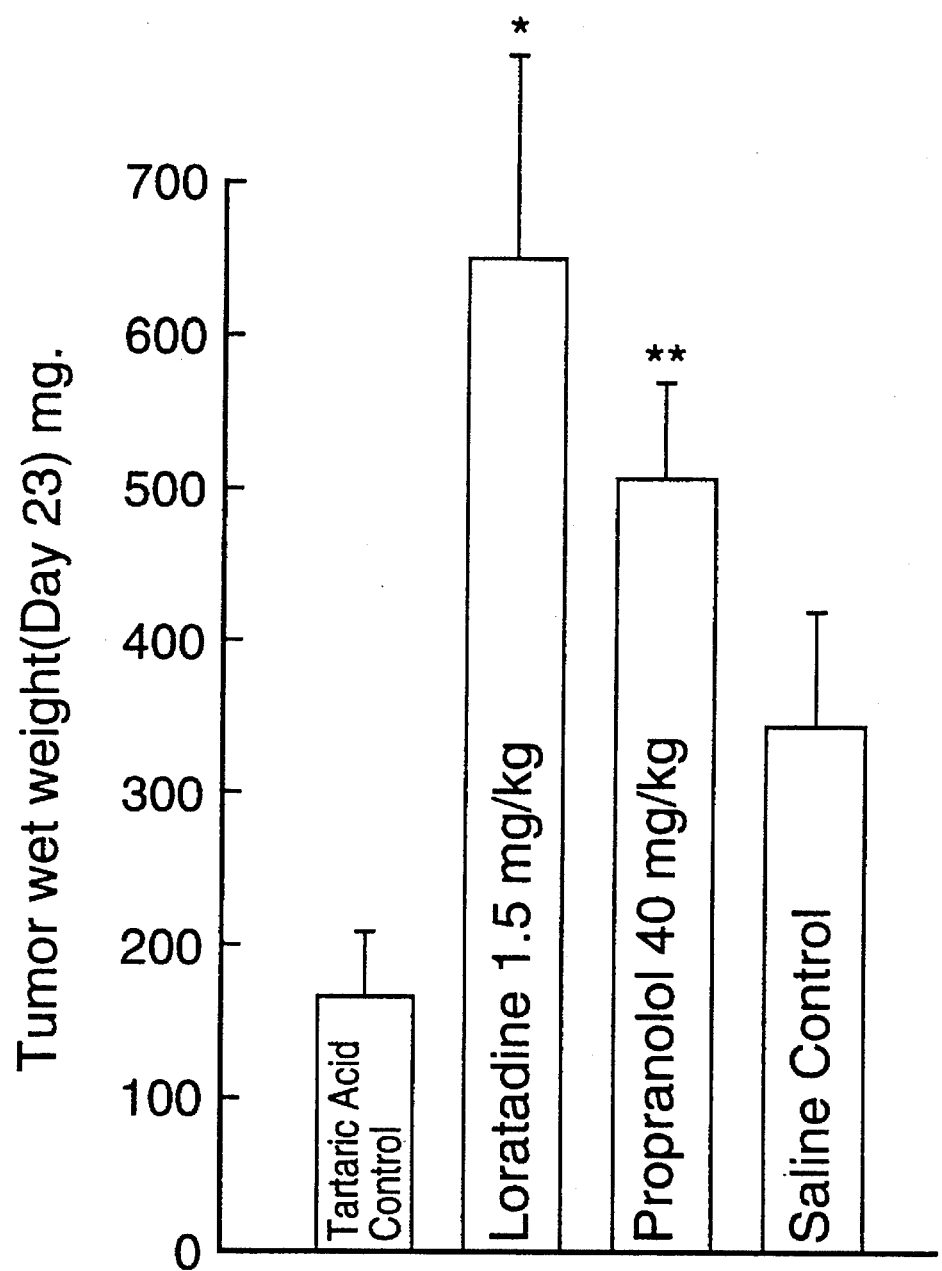
Figure 13:
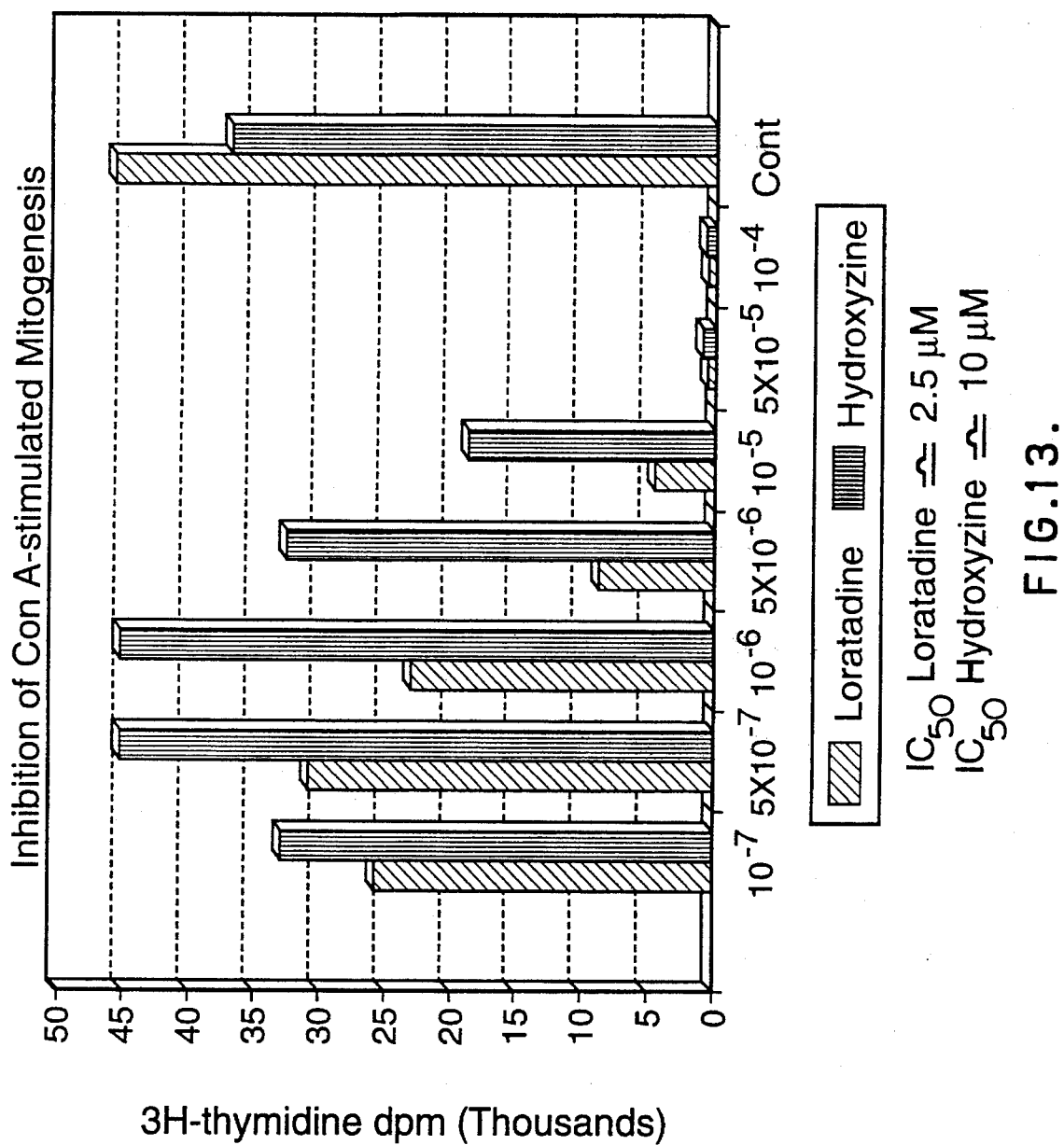

FIG. 11A shows that propanolol (a β-adrenergic antagonist) inhibits histamine binding to H$_{IC}$ in microsomes and FIG. 11B shows that propanolol inhibits normal lymphocyte mitogenesis. In a C-3 fibrosarcoma murine model, propanolol significantly increased tumor weight on Day 23, as seen in FIG. 12. Similarly loratidine (a tricyclic non-sedating H$_1$-antihistamine) potently promoted tumor growth, as seen in FIG. 12 and also inhibited concanavalin A-stimulated mitogenesis (FIG. 13). Astemizole (a non-sedating H$_1$-antihistamine) similarly is potent to inhibit histamine binding and concanavalin A-stimulated mitogenesis (data not shown) and, in two separate experiments, to potently stimulate the growth of C-3 fibrosarcoma, as shown in FIG. 14.

The compounds for which binding and proliferation data are provided in this Example, therefore, mimic the profiles of DPPE to inhibit normal cell proliferation but to promote malignant cell proliferation (Example IV). On the basis of his profile, these agents, at the proper dose level, may be predicted to increase the therapeutic index of chemotherapy drugs.

SUMMARY OF DISCLOSURE

In summary of this disclosure, the present invention provides a novel approach to chemotherapeutic treatment of cancer whereby an enhanced in vivo effect of the chemotherapeutic agent is obtained while achieving protection of normal cells, particularly bone marrow and gastro-intestinal cells, from the toxic effects of the chemotherapeutic agent. Modifications are possible within the scope of this invention.

What I claim is:

1. A method of protecting normal bone marrow cells in an animal from the adverse effects of chemotherapy, which comprises:

administering to said animal at least one diphenyl compound of the formula:

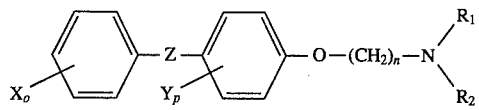

wherein X and Y are each fluorine, chlorine or bromine, Z is an alkylene group of about 1 to 3 carbon atoms or =C=O, or the phenyl groups are joined to form a tricyclic ring, o and p are 0 or 1, R$_1$ and R$_2$ are each groups containing 1 to 3 carbon atoms or are joined together to form a hetero-ring with the nitrogen atom and n is 1, 2 or 3, in an amount of from about 8 to about 240 mg/M$^2$ of animal for about 60 to about 90 minutes prior to commencement of said chemotherapy.

2. The method of claim 1 wherein, following said chemotherapy, said diphenyl compound is administered in a daily amount of from about 30 to about 1200 mg/M$^2$ of animal, so as to ameliorate adverse side effects of said chemotherapy.

3. A method for protecting normal cells lining the gastrointestinal tract from the adverse effects of chemotherapy, which comprises:

administering to said animal at least one diphenyl compound of the formula:

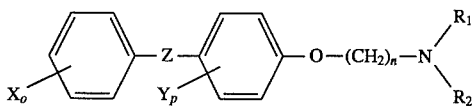

wherein X and Y are each fluorine, chlorine or bromine, Z is an alkylene group of about 1 to 3 carbon atoms or =C=O, or the groups are joined to form a tricyclic ring, o and p are 0 or 1, R$_1$ and R$_2$ are each groups containing 1 to 3 carbon atoms or are joined together to form a hetero-ring with the nitrogen atom and n is 1, 2 or 3, in an amount of from about 8 to about 30 mg/M$^2$ of animal for about 30 to about 90 minutes prior to commencement of said chemotherapy.

4. The method of claim 3 wherein, following said chemotherapy, said diphenyl compound is administered in a daily amount of from about 8 to about 12 mg/kg of animal, so as to ameliorate adverse side effects of said chemotherapy.

5. The method claimed in claim 1 or 3 wherein said at least one diphenyl compound is DPPE.

6. The method of claim 5 wherein said chemotherapy is effected using adriamycin.

* * * * *